(12) United States Patent
Tsuji et al.

(10) Patent No.: US 11,045,156 B2
(45) Date of Patent: Jun. 29, 2021

(54) METHOD FOR PERIODONTAL DISEASE MEASUREMENT

(75) Inventors: Hironobu Tsuji, Tokyo (JP); Akitoshi Katsumata, Gifu (JP); Shinya Saito, Tokyo (JP); Vladimir Volevich, Tokyo (JP); Kazuhumi Suzuki, Tokyo (JP)

(73) Assignee: Media Co., Ltd., Tokyo (JP)

( * ) Notice: Subject to any disclaimer, the term of this patent is extended or adjusted under 35 U.S.C. 154(b) by 425 days.

(21) Appl. No.: 14/235,492

(22) PCT Filed: Jul. 12, 2012

(86) PCT No.: PCT/JP2012/067825
§ 371 (c)(1),
(2), (4) Date: Mar. 14, 2014

(87) PCT Pub. No.: WO2013/018522
PCT Pub. Date: Feb. 7, 2013

(65) Prior Publication Data
US 2014/0234796 A1    Aug. 21, 2014

(30) Foreign Application Priority Data

Jul. 29, 2011  (JP) .............................. JP2011-166696

(51) Int. Cl.
*A61C 19/04*  (2006.01)
*A61B 6/14*  (2006.01)
*A61B 6/03*  (2006.01)

(52) U.S. Cl.
CPC ................ *A61B 6/14* (2013.01); *A61B 6/032* (2013.01); *A61C 19/04* (2013.01)

(58) Field of Classification Search
CPC .. A61C 19/04; A61B 6/14; A61B 6/03; A61B 6/032
See application file for complete search history.

(56) References Cited

U.S. PATENT DOCUMENTS

| 7,343,305 B2 * | 3/2008 | Benn ...................... A61C 19/00 433/215 |
| 2008/0226150 A1 | 9/2008 | Sadakane |
| 2013/0094740 A1 * | 4/2013 | Vandenberghe ......... A61B 6/14 382/131 |

FOREIGN PATENT DOCUMENTS

| JP | 11-047095 | 2/1999 |
| JP | 2001-061873 | 3/2001 |

(Continued)

OTHER PUBLICATIONS

International Search Report dated Sep. 25, 2012 filed in PCT/JP2012/067825.

(Continued)

*Primary Examiner* — Ralph A Lewis
(74) *Attorney, Agent, or Firm* — Rankin, Hill & Clark LLP (57) ABSTRACT

The method for periodontal disease measurement of the present invention includes: using a plurality of cross-sectional images provided by x-ray CT images of teeth and periodontal tissues to detect a contour of each tooth in each cross-sectional image, detect a dentition, and provide a dental formula; detecting the positions of the root apex, the alveolar crest, and the crown of each tooth from the detected tooth contour data; calculating at least one of a distance indicator, a volume indicator, a surface area indicator, a first moment indicator, a center-of-gravity indicator, and an alveolar bone indicator from the detected tooth contour data, and the position data of the root apex, the alveolar crest, and the crown of the tooth; and measuring the progression of periodontal disease based on at least one calculated indicator.

7 Claims, 7 Drawing Sheets

(56) References Cited

FOREIGN PATENT DOCUMENTS

| | | |
|---|---|---|
| JP | 2001-333898 | 12/2001 |
| JP | 2008-237895 | 10/2008 |
| JP | 2009-226016 | 10/2009 |
| JP | 2009-226096 | 10/2009 |
| JP | 2011-072573 | 4/2011 |
| JP | 2011-098047 | 5/2011 |

OTHER PUBLICATIONS

Office Action dated Sep. 30, 2014 for the corresponding Japanese Patent Application No. 2013-526801 and its English translation.
Extended European Search Report dated Feb. 24, 2015 for corresponding EP Patent Application No. 12820710.7.
Office Action dated Jun. 13, 2019 for corresponding EP Patent Application No. 12820710.7.

* cited by examiner

METHOD FOR PERIODONTAL DISEASE MEASUREMENT

TECHNICAL FIELD

The present invention relates to a method for periodontal disease measurement. More specifically, the present invention relates to a method for measuring the progression of periodontal disease based on a two-dimensional image of an x-ray CT image of the teeth.

BACKGROUND ART

Periodontal disease is a disease that affects a cementum portion around the teeth, in other words, the gingiva (gums), the alveolar bone, the periodontal ligament, and the root surface. However, generally, periodontal disease indicates an inflammatory disease affecting around the teeth. The disease occupies 90% or more of patients. Therefore, a common periodontal disease is caused by microorganisms called periodontal bacteria such as Porphyromonas gingivalis. The present invention also mainly targets the common periodontal disease. Hereinafter, the common periodontal disease is referred to as the "periodontal disease," and a periodontal disease other than the common periodontal disease is referred to as the "special periodontal disease."

Figure 3:
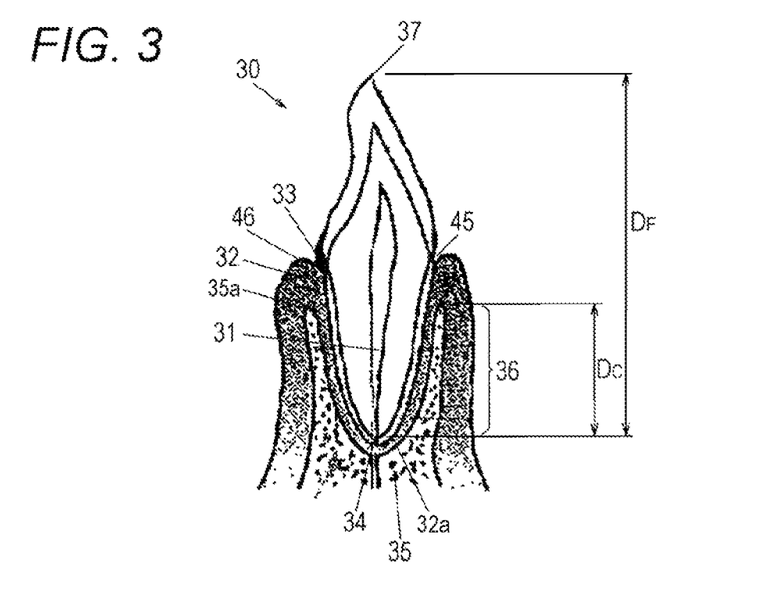
FIG. 3 schematically illustrates a cross section of a normal tooth.
Figure 4:
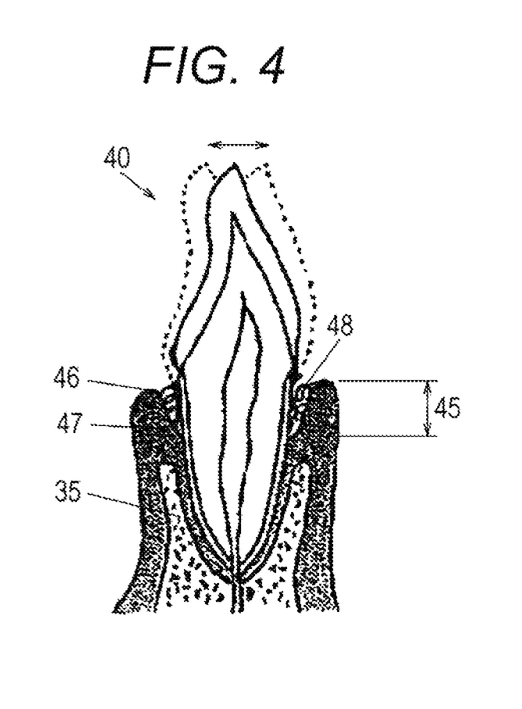
FIG. 4 schematically illustrates a cross section of a tooth affected by periodontal disease.

Hereinafter, the progression of the periodontal disease will be described, taking an example of a tooth in the mandible, the root apex of which points downward when a person is standing. The same shall apply to a tooth in the maxilla. FIG. 3 is a cross-sectional view schematically illustrating a normal tooth. FIG. 4 is a cross-sectional view schematically illustrating a tooth affected by the periodontal disease. As illustrated in FIG. 3, a normal tooth 30 has a root 31 supported by a periodontal ligament 32a, an alveolar bone 35, and a gingiva (or gums) 32. Moreover, between the root 31 and the gingiva 32 is called a periodontal pocket (or simply "pocket" or "gingival sulcus") 45. If affected by the periodontal disease, inflammation as in FIG. 4 is caused in the gingiva 32 and the periodontal ligament 32a to cause bleeding and pus discharge 48 in the periodontal pocket 45. Furthermore, the alveolar bone 35 starts to be resorbed and retracted. The depth of the pocket 45 from a gingival apex 46 to a pocket bottom 47 is approximately 0 to 1 mm in the healthy tooth 30. The depth of a tooth 40 affected by the periodontal disease is increasingly deepened with the progress of the periodontal disease.

Upon the start of the treatment of the periodontal disease, the current symptom is measured first to find the degree of the disease progression. How the symptom progresses needs to be then diagnosed. Up to the present time, various measurements have been developed. Examples of current major measurements include a measurement by probing, a measurement using intraoral radiography or panoramic x-ray imaging, and a measurement using a bacteriological examination. Furthermore, upon measurement, it is necessary to also consider individual differences in the forms of the root and the alveolar bone, individual differences in occlusion, and the like.

The probing measurement is a method for measuring the state of the symptom while introducing a probe (a needle for examination) into the pocket 45 and measuring the depth of the pocket 45, and is the simplest method. This method is superior in a respect of being applicable to symptoms at all stages. However, the measurement results vary depending on the skill level of an examiner. Moreover, especially in a severe case, there is a problem in causing pain to a patient since the probe stimulates the nerve. In other words, in the measurement of the depth of the pocket 45, a probe (a needle for measurement, or specifically, a needle calibrated with markings called a pocket probe) is introduced until reaching the lower end of the pocket. For one tooth 40, the measurement is performed at approximately six points and may involve bleeding. The measurement causes pain to a patient and takes time and effort. Moreover, there is a problem in that it may be insufficient as an objective indicator of the periodontal disease. In other words, even if the pockets 45 have the same depth, the volume of the tooth 40 below the pocket 45 varies depending on the tooth 40 or varies from person to person. In other words, the force supporting the tooth 40 cannot be determined only from the depth of the pocket 45.

The measurement using intraoral radiography or panoramic x-ray imaging is a method where the bone level and the external shape of the alveolar bone 35 are grasped from an x-ray of the (three-dimensional) tooth 40 and periodontal tissue to make a measurement. How much the tooth 40 is supported by the alveolar bone is measured based on the bone level and the external shape of the alveolar bone 35. This method is superior to the probing method in that reading can be performed with higher accuracy. However, the method cannot be used at the initial stage where the pocket 45 has just been formed, and cannot be used frequently. Moreover, there is a problem that if an x-ray image is unclear, accuracy is reduced.

Moreover, the measurement using a bacteriological examination is a method where the causative bacteria of periodontal inflammation are examined to measure the activity/progressiveness of the periodontal disease. In other words, it is considered that the degree of pathogenicity depends on the species of bacteria. The activity can be therefore determined by identifying the species of bacteria. However, the identification of bacterial species involves the problem of time and cost and is not simple.

In order to deal with such problems, a remaining teeth prediction system is proposed (Patent Literature 1). The prediction system evaluates a reduction in root surface area from the total surface area of currently effective roots, and the result is then used to predict a reduction in the number of remaining teeth. In this measurement, a reduction in the total surface area of effective roots is represented by a curve or a straight line to predict the number of remaining teeth, which can be easily figured out. Moreover, the method has an advantage that the result can be used as a material for long-term teeth prevention, treatment, and instruction. However, the root surface area is hardly obtained with high accuracy because of being calculated from a probing attachment level (the ratio of a portion where the gingiva is attached to a tooth). Sufficient satisfaction cannot be always obtained in that the resorption of the alveolar bone is not considered.

Moreover, an electronic medical support apparatus is proposed (Patent Literature 2). This apparatus compares a plaque score, periodontal pocket depth, and tooth mobility with their past data to calculate the progression rate of the periodontal disease. Based on the progression rate, information on the progression prediction of the periodontal disease is displayed. The technology has an advantage that can cause a patient to recognize the importance of periodontal disease treatment by motivating the patient. However, it is not necessarily fully satisfying in a respect that alveolar bone resorption is not considered.

CITATION LIST

Patent Literatures

PATENT DOCUMENT 1: JP-A-2001-061873
PATENT DOCUMENT 2: JP-A-11-047095

SUMMARY OF THE INVENTION

Problems to be Solved by the Invention

The present invention has been made considering the above problems. An object of the present invention is to provide a method for periodontal disease measurement that can obtain an indicator indicating the symptoms of periodontal disease objectively, simply and highly accurately without causing pain to a patient. More specifically, an issue of the present invention is to provide the following method for periodontal disease measurement. In other words, the measurement can collect an indicator indicating the progression of periodontal disease of a patient by x-ray CT without causing pain to the patient and causing a dentist to spend time and effort, achieve a highly accurate calculation for obtaining an objective indicator, and improve the accuracy of automatic detection measurement.

Solutions to the Problems

The present invention provides the following method for periodontal disease measurements to achieve the aforementioned object.

A first measurement is a method for periodontal disease measurement including: using a plurality of cross-sectional images provided by x-ray CT images of teeth and periodontal tissues to detect a contour of each tooth in each of the cross-sectional images, detect a dentition, and provide a dental formula; detecting the positions of the root apex, the alveolar crest, and the crown of each tooth from the detected tooth contour data; calculating at least one of a distance indicator, a volume indicator, a surface area indicator, a first moment indicator, a center-of-gravity indicator, and an alveolar bone indicator from the detected tooth contour data, and the position data of the root apex, the alveolar crest, and the crown of the tooth; and measuring the progression of periodontal disease based on at least one calculated indicator.

A second measurement is a method for periodontal disease measurement according to the first measurement, wherein the distance indicator is a value calculated as a ratio DC/DF of a length DC of the root surrounded by the alveolar bone currently supporting the tooth to a tooth length DF calculated based on the data of the root apex, the alveolar crest, and the crown.

A third measurement is a method for periodontal disease measurement according to first measurement, wherein the volume indicator is a value calculated as a ratio VC/VF of volume VC of the root surrounded by the alveolar bone currently supporting the tooth to tooth volume VF calculated based on the data of the root apex, the alveolar crest, and the crown.

A fourth measurement is a method for periodontal disease measurement according to the first measurement, wherein the surface area indicator is a value calculated as a ratio SC/SF of a surface area SC of the root surrounded by the alveolar bone currently supporting the tooth to a tooth surface area SF calculated based on the data of the root apex, the alveolar crest, and the crown.

A fifth measurement is a method for periodontal disease measurement according to the first measurement, wherein the first moment indicator is a value calculated as a ratio MC/MF of a first moment MC of the root surrounded by the alveolar bone currently supporting the tooth to a first moment MF of the tooth calculated based on the data of the root apex, the alveolar crest, and the crown.

A sixth measurement is a method for periodontal disease measurement according to the first measurement, wherein the center-of-gravity indicator is a value calculated as a ratio GC/GF of the center of gravity GC of the root surrounded by the alveolar bone currently supporting the tooth to the tooth's center of gravity GF calculated based on the data of the root apex, the alveolar crest, and the crown.

A seventh measurement is a method for periodontal disease measurement according to the first measurement, wherein the contour of the tooth is determined by calculating the roundness of the tooth from the detected tooth contour data and comparing the roundness with a standard feature value.

An eighth measurement is a method for periodontal disease measurement according to the first measurement, wherein the centers of gravity of the teeth are obtained from the detected tooth contour data, a curve passing around the obtained centers of gravity of the respective teeth is obtained, and the contour of the tooth is determined by the curve.

A ninth measurement is a method for periodontal disease measurement according to the first measurement, wherein the contour is determined by a CT image adjacent to a cross section photographed by the x-ray CT apparatus.

A tenth measurement is a method for periodontal disease measurement according to the first measurement, wherein the root apex, the alveolar crest, and the crown are determined by standard feature values and corresponding portions of another tooth in the vicinity.

An eleventh measurement is a method for periodontal disease measurement according to the first measurement, wherein the alveolar crest is determined by the alveolar bone around the contour.

A twelfth measurement is a method for periodontal disease measurement according to the first measurement, wherein the dentition is determined by referring to a reference dentition pattern.

A thirteenth measurement is a method for periodontal disease measurement according to the first measurement, further comprising, upon detecting a dentition and providing a dental formula, projecting the dentition on a curved surface along the dentition to create and display a panoramic image, and superimposing and displaying the dental formula thereon.

A fourteenth measurement is a method for periodontal disease measurement according to the thirteenth measurement, wherein the curved surface is a curved surface parallel to a tooth axis.

A fifteenth measurement is a method for periodontal disease measurement according to the first measurement, wherein the dental formula is displayed using a plurality of different colors.

A sixteenth measurement is a method for periodontal disease measurement according to the first measurement, further comprising, upon determining the degree of a disease of teeth and periodontal tissues based on the indicator, comparing the indicator with an indicator previously obtained.

Effects of the Invention

The present invention can obtain an effect where an indicator indicating the state of periodontal disease objectively can be obtained simply and highly accurately without causing pain to a patient. More specifically, the present invention can obtain the following effects. In other words, it becomes possible to collect an indicator indicating the progression of periodontal disease of a patient by x-ray CT without causing pain to the patient and causing a dentist to spend time and effort, achieve a highly accurate calculation for obtaining an objective indicator, and improve the accuracy of automatic detection measurement.

DESCRIPTION OF EMBODIMENTS

Figure 1:
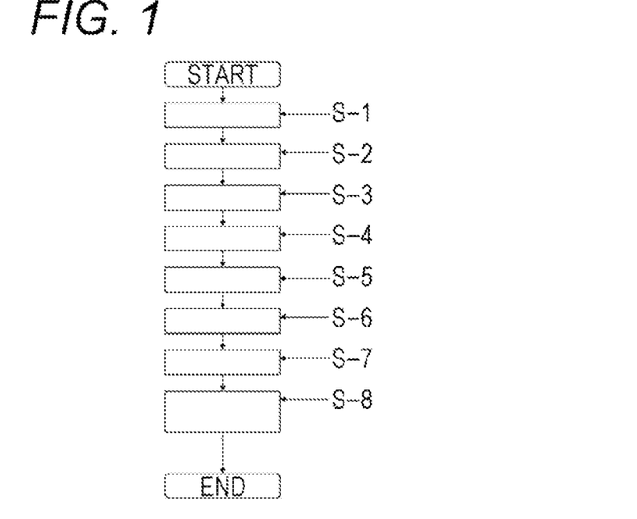
FIG. 1 is a flowchart illustrating a method for periodontal disease measurement according to an embodiment of the present invention.
Figure 2:
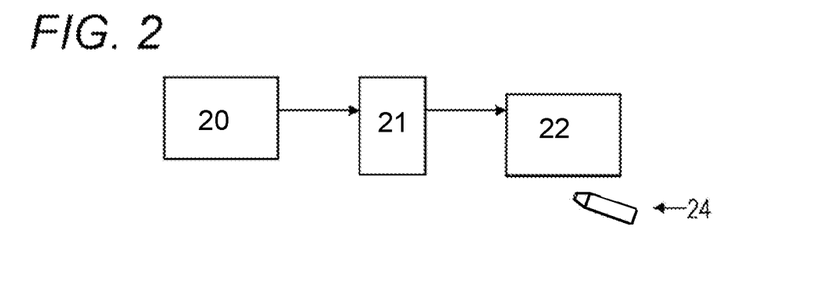
FIG. 2 schematically illustrates an apparatus that is used for the method for periodontal disease measurement according to the embodiment of the present invention and connected to an x-ray imaging apparatus, a computer, and an image display device.

Hereinafter, an embodiment of the present invention will be described with reference to the drawings. FIG. 1 is a flowchart illustrating a method for periodontal disease measurement according to the embodiment of the present invention. FIG. 2 is a diagram illustrating an apparatus that is used for the method for periodontal disease measurement according to the embodiment of the present invention and connected to a dental x-ray imaging apparatus, a computer, and an image display device.

As illustrated in FIG. 1, in the method for periodontal disease measurement of the present invention, the teeth of an animal such as a human or dog are photographed by dental radiography to obtain a plurality of x-ray CT images. The plurality of obtained CT images is read in one by one to be displayed (Step S-1). A midline is detected on the displayed CT image (Step S-2). The contour of each tooth is detected on each CT image (Step S-3). The contour of each tooth is detected between the CT images (Step S-4). A dental formula is provided (Step S-5). The root apex, the alveolar crest, and the crown are detected (Step S-6). The detection result is displayed (Step S-7). Based on data on the detected root apex, alveolar crest, and crown, at least one of a distance indicator, a volume indicator, a surface area indicator, a first moment indicator, and a center-of-gravity indicator is calculated (Step S-8). The progression of periodontal disease is measured based on at least one calculated indicator.

Moreover, as illustrated in FIG. 2, the method for periodontal disease measurement for measuring the progression of periodontal disease according to the present invention uses, for example, a system connected to an x-ray CT imaging apparatus 20, a computer (PC) 21, and an image display device (monitor) 22. The x-ray CT imaging apparatus 20 photographs the teeth of a patient. The computer (PC) 21 automatically detects the root apex, the alveolar crest, and the crown from a two-dimensional image obtained by capturing the photographed x-ray CT image and displays the result on the image display device (monitor) 22. If there is an error in detection, a correction instruction is given by, for example, a light pen 24 on the displayed image. An instruction may be given by a cursor instead of the light pen 24.

Hereinafter, the steps will be described in detail. Step S1 is a CT image processing step. In the method for periodontal disease measurement of the present invention, the teeth of a human or animal are photographed by x-ray CT first. Consequently, several tens to several hundreds of successive CT images of thin cross sections are obtained. The obtained CT images are captured one by one and displayed.

Figures 5A, 5B:
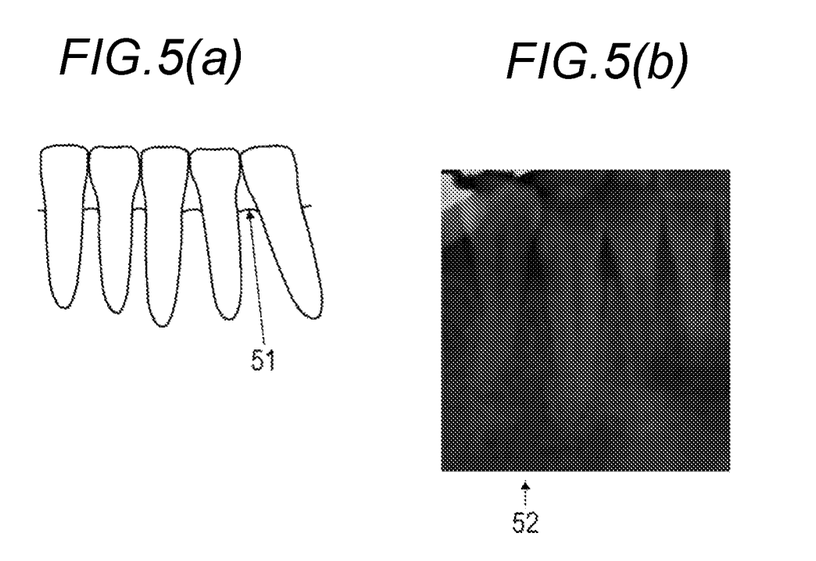
FIG. 5(a) is an explanatory view schematically illustrating the alveolar bone.
FIG. 5(b) is an x-ray CT image illustrating the alveolar bone.

The above-mentioned method is used to obtain successive cross-sectional x-ray CT images by photographing the teeth of a human or animal by x-rays. As illustrated in FIGS. 3, 4 and 5, an alveolar bone 51 is photographed but a gingiva 32 is hardly photographed in the x-ray CT images. A tooth 30 is supported by an alveolar bone 35 and the gingiva (gums) 32. A cervix 33 and a gingival apex 46 are aligned in the healthy tooth 30. The gingiva 32 is in close contact with the cervix 33 and supports the tooth 30. In a tooth 40 affected by periodontal disease, the gingiva pulls away from the tooth to form a pocket 45. Furthermore, bleeding and pus discharge 48 are caused in a severe case. The portion from the gingival apex 46 to the bottom of the pocket 45 cannot support the tooth 30. If periodontal disease progresses, the alveolar bone 35 is also resorbed and retracted. The force of the alveolar bone 35 and the gingiva 32 to support the tooth 40 is reduced.

Next, the obtained successive cross-sectional x-ray CT images are processed one by one. FIGS. 6(a) to 6(h) illustrate the plurality of obtained x-ray CT images of the teeth of the patient. The images represent progressively lower levels from (a) toward (h). FIGS. 6(a) to 6(h) illustrate examples of every 10 images from the 200th image to the 130th image among approximately 500 x-ray CT images photographed at intervals of 0.3 mm.

The x-ray CT image will be described here. The x-ray CT image is a tomographic image obtained by acquiring data using a computer and reconstructing an image. Especially, in the case of dental x-ray CT, it is possible to observe a fine cross-sectional image with little distortion by short-time x-ray irradiation. It is possible to accurately diagnose/examine hard tissues of the head and neck such as jaws, teeth, and oral region, and their surrounding tissues with a three-dimensional image. Hence, it exerts the effect on implant treatment and diagnosis/measurement/treatment of temporomandibular joint disease, a periapical lesion, and the like. Furthermore, since x-rays are irradiated for a short time, exposure is also reduced compared with conventional CT. Hence, safer and more secure treatment can be offered. The resolution of the apparatus is approximately 0.1 mm to 0.5 mm.

Hereinafter, the detection process will be described. The order of the steps may be changed. Moreover, not all the steps may be included. The order of detection is only an example.

Step S2 is the step of detecting a midline.

Figure 6:
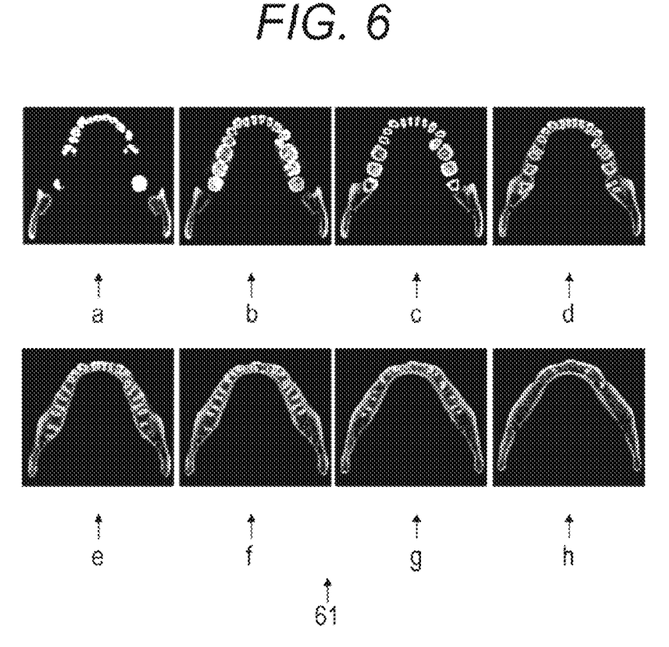
FIGS. 6(a) to 6(h) are a plurality of x-ray CT images of the teeth of a patient, and are images illustrating progressively lower levels from (a) toward (h).

The image (d) where all the teeth have been photographed is selected to detect a midline 71. Detection is automatically performed. Software on the computer 21 detects the center of the jawbone, the margin of a tooth, and the like, compares them with a reference dentition pattern 81 of FIG. 8, and the like, and determines and displays the midline 71. An operator checks the detection result, and if it is wrong, corrects the result on the image. A dental formula (the numbers of teeth) is noted by L1, L2, ..., R1, R2, ... in FIG. 7. At this stage, the dental formula is not automatically provided yet.

Step S3 is the step of detecting tooth contours in one image.

Figure 9:
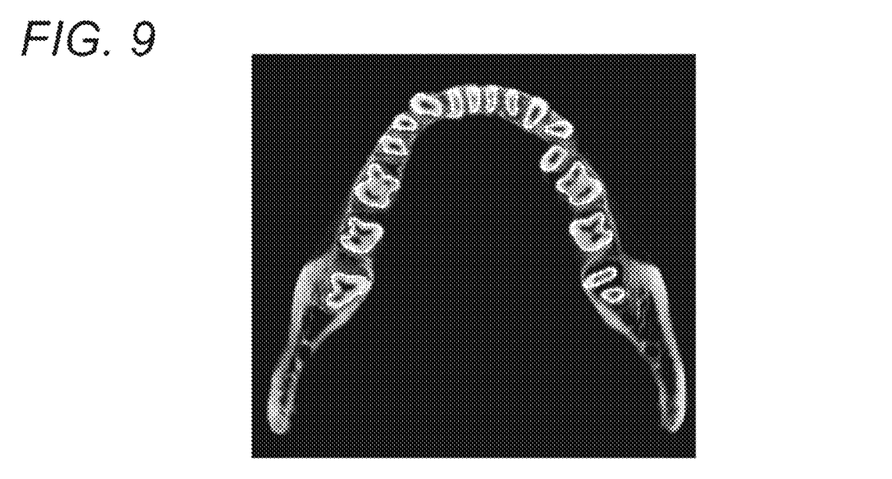
FIG. 9 illustrates an example of a contour detection result.

The software detects the contour of each tooth as illustrated in FIG. 9. Firstly, a process in one screen will be described. A contour is detected by contour tracking or the like. Then, the circumference L, inner surface area A, roundness (L2/A) of the contour are calculated and compared with the respective standard feature values to determine it as a tooth and conclude its shape. Examples of the standard feature values include the position of each tooth, a fact that tooth size is 15 mm or less, a fact that canine tooth is slightly larger, and a fact that teeth after tooth number six have a plurality of roots.

Next, a process of a relationship between adjacent teeth will be described. Assume that there are small, gradual differences in size, shape, and the like between the adjacent teeth and their changes are smooth. If they are not applicable, corrections are made or an alert is displayed. A tentative dental formula, L1, L2, ..., R1, R2, ... (FIG. 7), is provided here. Furthermore, if there are big differences in the positions, sizes, shapes, and the like of teeth corresponding to the dental formula after a comparison with the reference dentition pattern 81 (FIG. 8), corrections are made or an alert is displayed. If there is an error in the dental formula, the dental formula is also corrected. In other words, "the determination of a dentition by the reference dentition pattern" is achieved.

Figure 10:
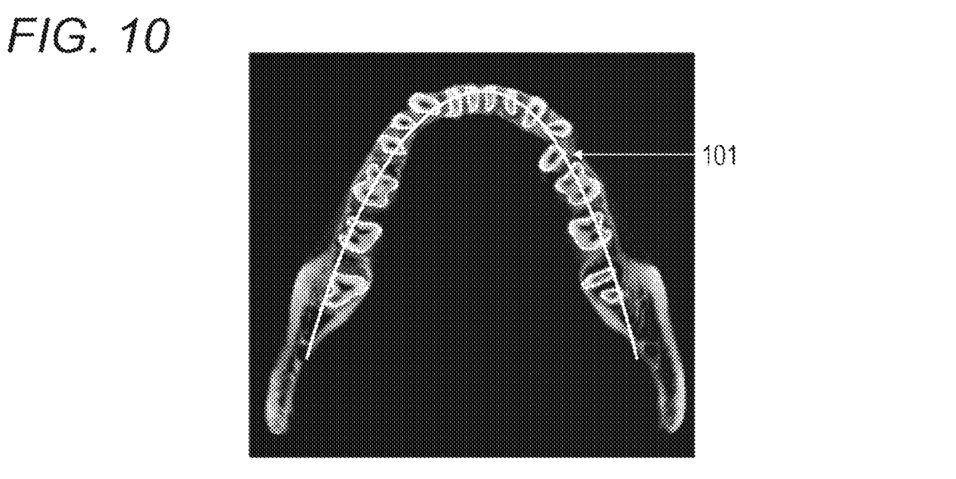
FIG. 10 illustrates a curve passing around the center of gravity of each tooth.

A method for creating and checking a connected curve will be described. As illustrated in FIG. 10, a spline curve 101 passing around the centers of gravity of the detected teeth is created. This is a method to correct the data if the teeth are not aligned on such a line. If each individual tooth deviates greatly from the curve 101, an average value of adjacent teeth is used to correct the data and display an alert.

In Step S4, tooth contour detection between images whose cross sections are adjacent is performed.

A process over a plurality of screens will be described. The software processes the CT images from a root apex 34 to a crown 37 one by one and detects the contours of the teeth as illustrated in FIGS. 11 to 15. FIGS. 11 to 15 respectively illustrate a tooth contour 111 of x-ray CT image numbers 192, 180, 170, 168, and 155. The contour 111 in FIGS. 11 to 15 indicates the contour of the tooth L7. Assume that there are small, gradual differences in the center of gravity, the circumference, the contour shape, and the like between adjacent CT images. If the changes are not smooth, they are corrected by the software and an alert is displayed. In other words, "determination by adjacent CT images" is achieved. The position where the contour cannot be detected is the root apex or the crown.

Figure 11:
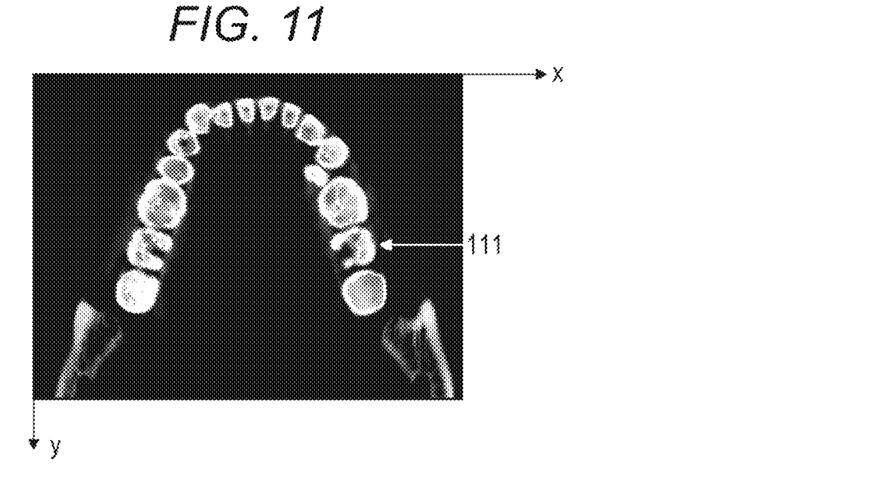
FIG. 11 illustrates a tooth contour of x-ray CT image number 192.
Figure 12:
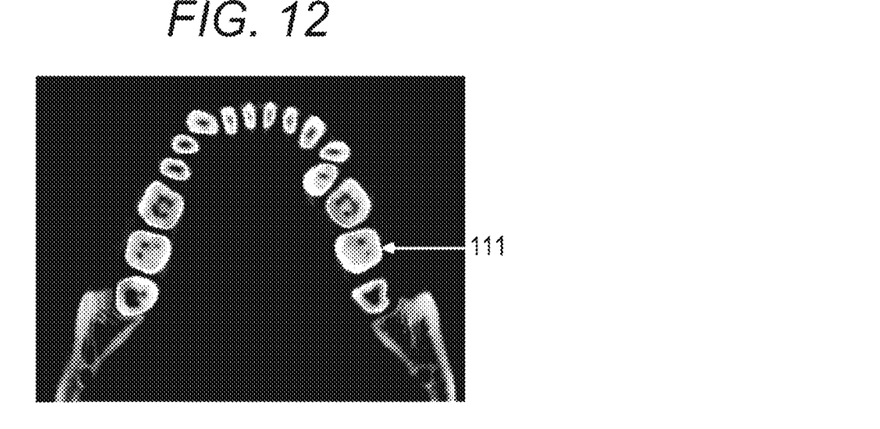
FIG. 12 illustrates the tooth contour of x-ray CT image number 180.

Generally, the position of the contour (root) shifts from its initial position because it moves diagonally as the x-ray CT images change. For the coordinate axes, the x-axis and y-axis are taken as illustrated in FIG. 11, and the z-axis is taken in a manner of being vertical with respect to the paper and facing the other way. Assuming that a line linking the center of gravity is referred to as the tooth axis, the tooth axis may not be parallel to the z-axis. The inclination of the tooth axis with respect to the z-axis is calculated to be used later for a correction of a distance calculation, a correction of display, and the like.

Step S5 is the step of providing a dental formula.

Figure 7:
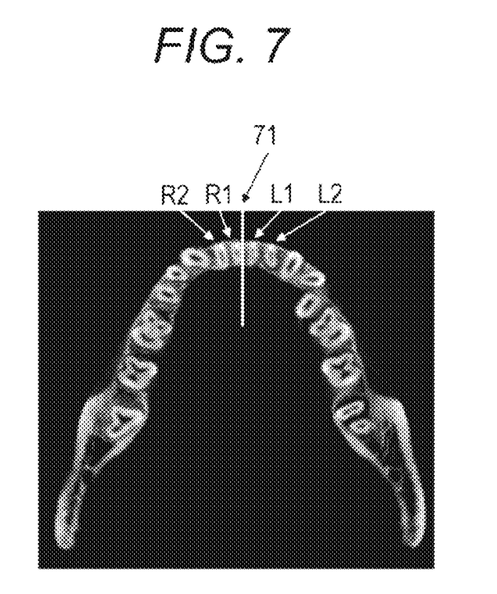
FIG. 7 illustrates a midline and a dental formula.
Figure 8:
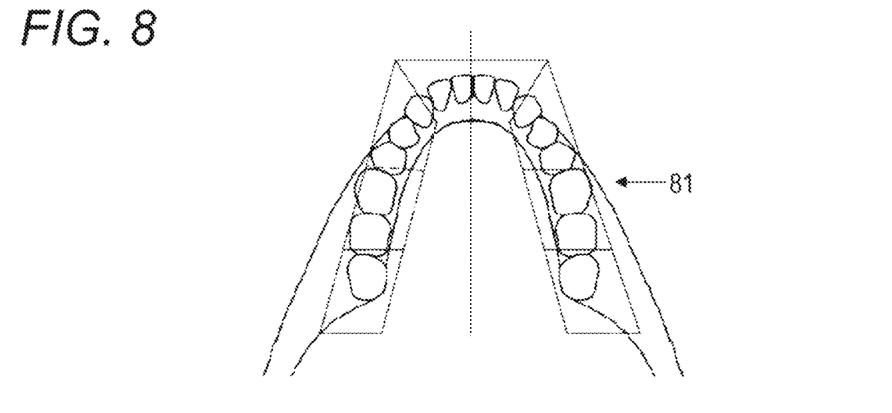
FIG. 8 illustrates a reference dentition pattern.

With the above steps, the contours of the teeth were detected and the dentition as the arrangement of teeth could be detected. A final dental formula determined from the result is provided as L1, L2, L3, ..., R1, R2, R3, ... as illustrated in FIG. 7, and is displayed. If there is an error, the error is corrected (by the operator).

Step S6 is the step of detecting the root apex, the alveolar crest, and the crown.

Data on the root apex, the alveolar crest, and the crown is detected. Detection is automatically performed. The detected data on the root apex, the alveolar crest, and the crown is displayed. The operator checks the detection result, and if it is wrong, a correction is made. The root apex is set to a position where the contour is no longer detected on the lower side. The crown is set to a position where the contour is no longer detected on the upper side. The alveolar crest is determined by the alveolar bone around the contour. For example, the alveolar crest is set to the topmost position within a designated width around the contour of the tooth in which the alveolar bone exists. Looking at 111 (L7) of FIG. 13 (CT image number 170), the alveolar bone is visible around the contour of the tooth. If the alveolar bone is not visible in the images with higher numbers than 170, the alveolar crest of L7 is 170. Similarly, the alveolar crest of each tooth is detected.

The alveolar crest may not be uniform around the tooth. Looking around the tooth 111 (L7) of number 170 in FIG. 13, the alveolar bone is visible on the upper, right, and lower sides, but is not visible in any other directions. The alveolar bone comes into sight also on the left side in number 168 in FIG. 14. In this manner, the heights of the alveolar crest are detected in a plurality of directions. Consequently, it is also possible to cover the measurement by generally measuring six points around a tooth by probing.

A description will be given about a method by making comparisons respectively with the positions of the root apex, the alveolar crest, and the crown of another adjacent tooth and determining the positions. This method assumes that the root apex, the alveolar crest, and the crown of the adjacent tooth are in substantially similar positions, and corrects data. If the positions of the root apex, the alveolar crest, and the crown are greatly different from those of the adjacent tooth, these positions are set to average values between the adjacent teeth, and an alert is displayed to prompt the operator to make corrections. In other words, "the determination of the root apex, the alveolar crest, and the crown by corresponding portions of another tooth in the vicinity" is achieved. Moreover, if these positions are compared with standard feature values (standard positions and the like) of each tooth, and found to be greatly different, it is also possible to display an alert and prompt the operator to make corrections. In other words, "the determination of the root apex, the alveolar crest, and the crown by the standard feature values" is achieved.

Step S7 is a result display step.

Figure 13:
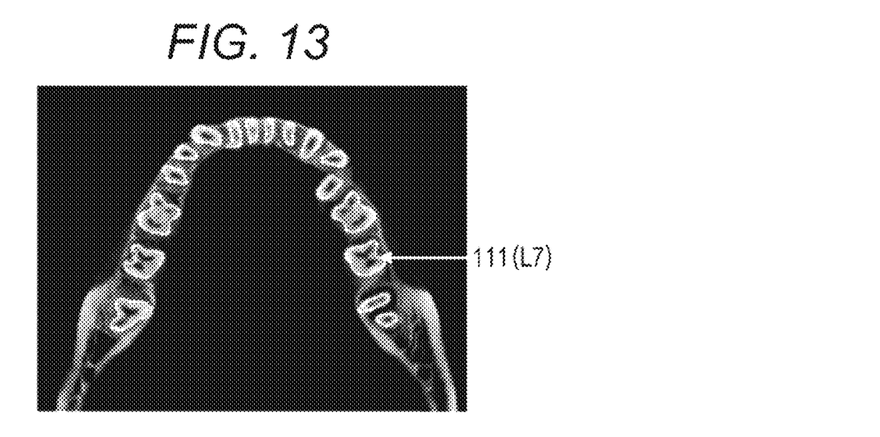
FIG. 13 illustrates the tooth contour of x-ray CT image number 170.
Figure 14:
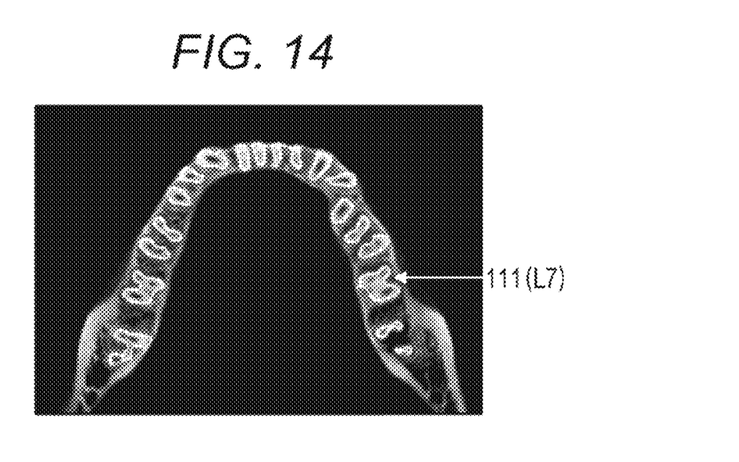
FIG. 14 illustrates the tooth contour of x-ray CT image number 168.
Figure 15:
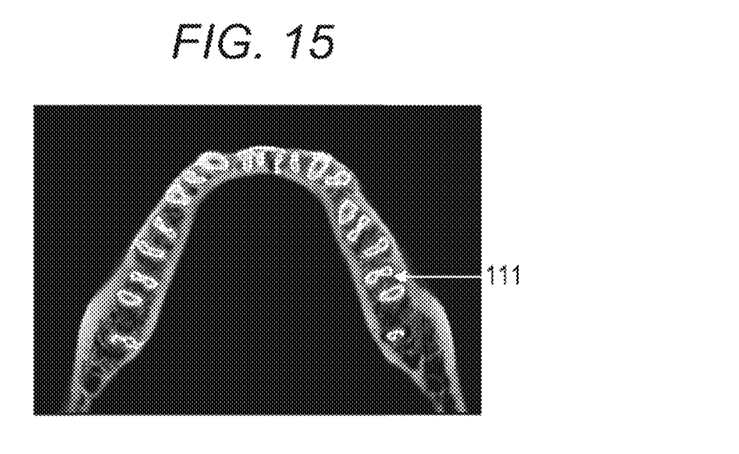
FIG. 15 illustrates the tooth contour of x-ray CT image number 155.
Figure 16:
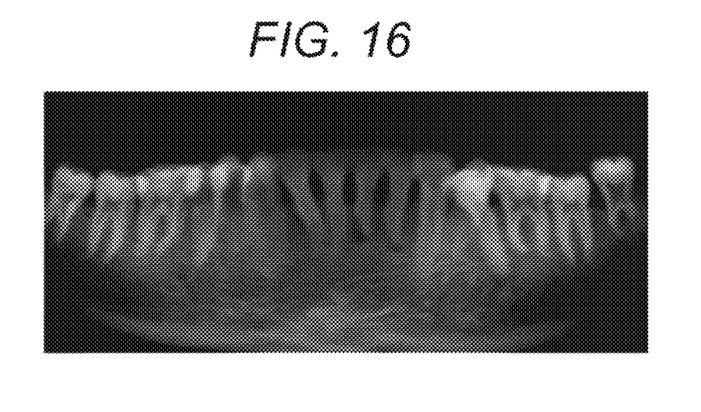
FIG. 16 illustrates a panoramic image projected on a curved surface passing around the center of gravity of each tooth.
Figure 17:
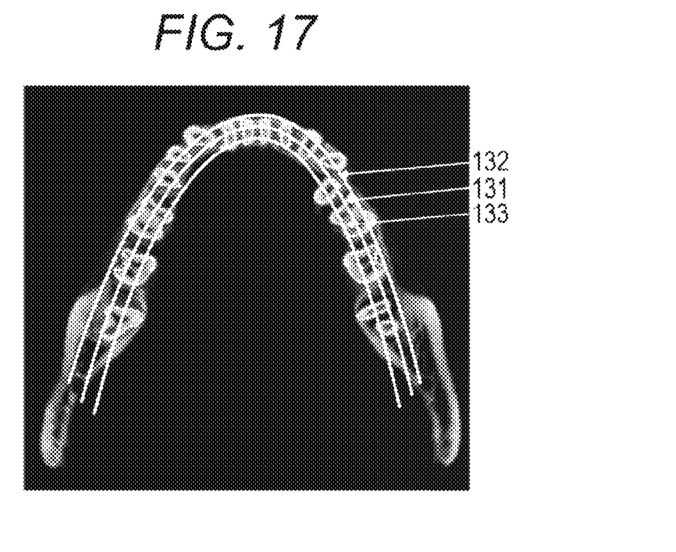
FIG. 17 illustrates a projected curved surface for creating a panoramic image.

The dentition is projected on a curved surface along the dentition based on the detected teeth to create a panoramic image and display the panoramic image as in FIG. 13. If the tooth axis is parallel to the z-axis, FIG. 16 is an image where the original image portion with the thickness of a fixed width from a curved surface 133 to a curved surface 132 parallel to a curved surface 131 parallel to the tooth axis (z-axis) passing around the positions of the detected teeth are projected on the curved surface 131 as illustrated in FIG. 17. If the tooth axis is not parallel to the z-axis, a correct length is projected by inclining the curved surface in agreement with the inclination of the tooth axis. As illustrated in FIG. 16, the tooth axis of an anterior tooth is not parallel to the z-axis in many cases. The correct length is projected by inclining the curved surface in agreement with the inclination of the tooth axis.

Figure 18:
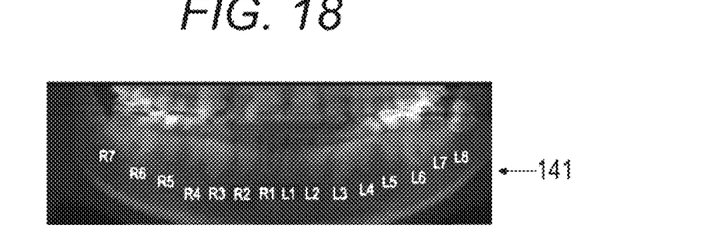
FIG. 18 illustrates an image on which a dental formula is superimposed on the panoramic image.

In the display of the result, specifically speaking, the cross sections of the detected teeth are superimposed on FIG. 16, and further, the dental formula is also superimposed and displayed as illustrated in FIG. 18. The dental formula is displayed using a plurality of different colors. For example, R1 and L1 are illustrated in blue, R2 and L2 in cyan, R3 and L3 in blue green, R4 and L4 in green, R5 and L5 in yellow green, R6 and L6 in orange, R7 and L7 in red, and R8 and L8 in magenta. There is no R8 in FIG. 18.

Step S8 is the step of calculating an indicator of a distance, the volume of the root, the surface area of the root, the first moment of the root, or the center of gravity.

At least one indicator of a distance indicator, a volume indicator, a surface area indicator, a first moment indicator, and a center-of-gravity indicator is calculated based on the detected data on the root apex, the alveolar crest, and the crown. In other words, the positions of the root apex, the alveolar crest, and the crown detected in Step S6, as well as the detected contour and the like, are used to calculate an indicator of at least one of a distance, volume, a surface area, a first moment, or the center of gravity. Hereinafter, each indicator will be described in turn.

(Method for Calculating Distance Indicator KD)

A distance indicator (root distance indicator) (KD) being an indicator of the state of a tooth can be calculated as follows. Prior to the calculation of the distance indicator (root distance indicator) (KD), an entire length (DF) of one tooth is calculated first as follows. In other words, a length from the root apex 34 to the crown 37 is set as the tooth length (DF).

This is calculated by the following equation: DF=the root apex−the crown, and is converted to an actual unit. If the tooth axis is not parallel to the z-axis, when the inclination from the z-axis is T degree, a correction is made by a mathematical equation (1).

[Math. 1]

$$D_F = D_F / \cos T \quad (1)$$

Next, a length (DC) of the root surrounded by the alveolar bone is calculated as follows. In other words, the length from an alveolar crest 35a to the root apex 34 is set as the length (DC) of the root surrounded by the alveolar bone.

This is calculated by the following equation: Dc=the root apex−the alveolar crest, and is converted to an actual unit. In this example, it is the number of images from x-ray CT image number approximately 220 to CT image number approximately 155. Moreover, when the inclination of the tooth axis is T degree, a correction is made by a mathematical equation (2).

[Math. 2]

$$D_C = D_C / \cos T \quad (2)$$

The distance indicator (root distance indicator) (KD) being the indicator of the state of a tooth is calculated as a ratio (DC/DF) of the length (DC) of the root surrounded by the alveolar bone currently supporting the tooth to the entire length (DF) of the tooth calculated from the above. In other words, the indicator (distance indicator) (KD) of the state of a tooth can be calculated by a mathematical equation (3).

[Math. 3]

$$K_D = D_C / D_F \quad (3)$$

(Method for Calculating Volume Indicator (Kv))

A volume indicator (root volume indicator) (Kv) being an indicator of the state of a tooth can be calculated as follows. Prior to the calculation of the volume indicator (root volume indicator) (Kv), the volume (VF) of the entire tooth is calculated first as follows. In other words, the volume from the root apex 34 to the crown is set as the volume (VF) of the tooth, and is calculated. For example, the contour is automatically detected in the x-ray CT image to calculate its area. This is continued from the root apex to the crown. The sum of them is set as the volume (VF). The area is the number of pixels surrounded by the contour. The summation of the number of pixels of the inside surrounded by the contour is performed. This is converted to an actual unit. In this case, the volume (VF) of the tooth can be calculated by a mathematical equation (4). A symbol "SUR" in the mathematical equation (4) indicates the area in the contour of the tooth on a (x, y) coordinate plane with the z-coordinate of z. A symbol "HA" indicates the z-coordinate of the root apex 34. A symbol "HC" indicates the z-coordinate of the crown. The same shall apply below. In terms of the volume (VF) of the tooth, the numbers of pixels may be summed and converted to an actual unit.

[Math. 4]

$$V_F = \int_{HA}^{HC} dz \iint_{SUR} dx dy \quad (4)$$

Next, the volume (VC) of the root surrounded by the alveolar bone currently supporting the tooth is calculated as follows. In other words, the volume (VC) of the root of a region 36 surrounded by the alveolar bone from the alveolar crest 35a to the root apex 34 is calculated. The contours from x-ray CT image number approximately 220 to CT image number approximately 155 are automatically detected to calculate their areas. In this case, the volume (VC) of the root surrounded by the alveolar bone can be calculated by a mathematical equation (5). A symbol "HB" indicates the z-coordinate of an alveolar crest 35a.

[Math. 5]

$$V_C = \int_{HA}^{HB} dz \iint_{SUR} dxdy \quad (5)$$

The volume indicator (root volume indicator) (Kv) being the indicator of the state of a tooth can be calculated from a ratio (VC/VF) of the volume (VC) of the root surrounded by the alveolar bone currently supporting the tooth to the entire volume (VF) of the tooth calculated from the above. In other words, the indicator (root volume indicator) (Kv) of the state of a tooth can be calculated by a mathematical equation (6).

[Math. 6]

$$K_V = V_C/V_F \quad (6)$$

The value of the volume indicator (root volume indicator) ranges from 0 to approximately 0.5, and is large in a healthy condition. For example, assume that a tooth is healthy with KV of down to approximately 0.4. The value, 0.4, is an interim value. The value is to be inspected by many examples and determined. The progression of periodontal disease can be measured based on the indicator calculated in this manner.

(Method for Calculating Surface Area Indicator (KS))

A surface area indicator (root surface area indicator) (KS) being an indicator of the state of a tooth can be calculated as follows. Prior to the calculation of the surface area indicator (root surface area indicator) (KS), a root surface area (S) can be calculated by a mathematical equation (7) first. An upper limit of integration by the equation is set to the crown to calculate an entire surface area (SF) of the tooth. An upper limit of integration is set to the alveolar crest to calculate a surface area (SC) of the root surrounded by the alveolar bone. The root surface area can also be substituted by the summation of the contour length of the x-ray CT image. The root surface area is not the contour length in a strict sense. However, it does not make a big difference even if a calculation is strictly made, and the substitution is therefore possible. A symbol "CON" of the mathematical equation (7) indicates a region, the length of which is calculated, in other words, the contour line of a tooth sectioned on the (x, y) coordinate plane with the z-coordinate of z.

[Math. 7]

$$S = \int_{HA}^{HT} dz \int_{CON} \sqrt{1 + \left(\frac{dy}{dx}\right)^2} dx \quad (7)$$

The surface area indicator (root surface area indicator) (KS) being the indicator of the state of a tooth can be calculated from a ratio (SC/SF) of the surface area (SC) of the root surrounded by the alveolar bone currently supporting the tooth to the entire surface area (SF) of the tooth calculated from the above. In other words, the surface area indicator (root surface area indicator) (KS) being the indicator of the state of a tooth can be calculated by a mathematical equation (8).

[Math. 8]

$$K_S = S_C/S_F \quad (8)$$

The value of the surface area indicator KS also ranges from 0 to approximately 0.5. The larger the surface area is, the healthier the tooth is. The progression of periodontal disease can be measured based on the indicator calculated in this manner.

(Method for Calculating First Moment Indicator (KM))

A first moment indicator (root first moment indicator) (KM) being an indicator of the state of a tooth can be calculated as follows. Prior to the calculation of the first moment indicator (root first moment indicator) (KM), a first moment (M) can be calculated by the summation of the area of the x-ray CT image times the length from the root apex. In other words, the indicator can be calculated by a mathematical equation (9). An upper limit of integration by the equation is set to the crown to calculate all first moments (MF) of the tooth. An upper limit of integration is set to the alveolar crest to calculate the first moment (MC) of the root surrounded by the alveolar bone.

[Math. 9]

$$M = \int_{HA}^{HT} zdz \iint_{SUR} dxdy \quad (9)$$

The first moment indicator (root first moment indicator) (KM) being the indicator of the state of a tooth can be calculated from a ratio (MC/MF) of the first moment (MC) of the root surrounded by the alveolar bone currently supporting the tooth to all the first moments (MF) of the tooth calculated from the above. In other words, the first moment indicator (root first moment indicator) (KM) being the indicator of the state of a tooth can be calculated by a mathematical equation (10).

[Math. 10]

$$K_M = M_C/M_F \quad (10)$$

The value of the first moment indicator KM also ranges from 0 to approximately 0.5. The larger the surface area is, the healthier the tooth is. The progression of periodontal disease can be measured based on the indicator calculated in this manner.

(Method for Calculating Center-of-Gravity Indicator (KG))

A center-of-gravity indicator (a root center-of-gravity indicator) (KG) being an indicator of the state of a tooth can be calculated as follows. Prior to the calculation of the center-of-gravity indicator (root center-of-gravity indicator) (KG), the center of gravity (G) of the tooth is one obtained by dividing the first moment by mass. The mass is the product of the volume times the density. However, since the denominator and the numerator are multiplied by the density, it can be ignored. In other words, the center of gravity can be calculated by the following equation 11. The center of gravity (GC) of the root surrounded by the alveolar bone can be calculated by having an index of the equation (11) of C.

[Math. 11]

$$G_F = M_F/V_F \quad (11)$$

The center-of-gravity indicator (root center-of-gravity indicator) (KG) being the indicator of the state of a tooth can be calculated from a ratio (GC/GF) of the center of gravity (GC) of the root surrounded by the alveolar bone currently supporting the tooth to the tooth's center of gravity (GF) calculated from the above. In other words, the center-of-gravity indicator (root center-of-gravity indicator) (KG) being the indicator of the state of a tooth can be calculated by a mathematical equation (12).

[Math. 12]

$$K_G = G_C/G_F \tag{12}$$

The value of the center-of-gravity indicator KG also ranges from 0 to approximately 0.5. The larger the surface area is, the healthier the tooth is. The progression of periodontal disease can be measured based on the indicator calculated in this manner.

In the present invention, at least one of the above-mentioned indicators is used to measure the progression of periodontal disease. Moreover, the indicator is compared with an indicator obtained in the previous measurement and accordingly it is possible to check the validity of the indicator, the speed of progression, and the like. It is preferred that a combination of indicators to be adopted be determined by considering various things such as a measurement time and measurement accuracy. Moreover, another indicator such as an indicator based on the depth of a periodontal pocket or another method may be combined and used.

DESCRIPTION OF REFERENCE SIGNS

20 X-ray imaging apparatus
21 Computer (PC)
22 Image display device (monitor)
24 Pen light
30 Tooth
31 Root
32 Gingiva (gums)
32a Periodontal ligament
33 Cervix (curvature change point)
34 Root apex
35 Alveolar bone
35a Alveolar crest
36 Region surrounded by the alveolar bone
40 Tooth
45 Pocket (Gingival sulcus)
46 Gingival (gum) apex
47 Pocket bottom
48 Bleeding and pus discharge
51 Alveolar bone
52 Two-dimensional x-ray image
71 Midline
81 Reference dentition pattern
101 Curve
111 Contour
131 Curved surface
132 Curved surface
133 Curved surface
L1 to L8 Dental formula
R1 to R8 Dental formula

The invention claimed is:

1. A method for periodontal disease measurement by making use of a system connected to an x-ray CT imaging apparatus, a computer, and an image display device, comprising:

photographing teeth and periodontal tissues with the x-ray CT imaging apparatus to produce a plurality of cross-sectional X-ray CT images of teeth and periodontal tissues;

automatically detecting position data of a root apex, an alveolar crest, and a crown of each tooth by first detecting a contour of each tooth in each of the plurality of cross-sectional X-ray CT images, by second detecting a dentition, said first detecting and said second detecting being done one by one for each of said cross-sectional X-ray CT images, the first detecting being done by software on the computer by calculating circumference, inner surface area, and roundness of the contour and by comparing resulted data of the calculation with standard feature values to determine as a tooth, the root apex being set to a position where the contour is no longer detected on the lower side, the crown being set to a position where the contour is no longer detected on the upper side, the alveolar crest being set to the topmost position within a designated width around the contour of the tooth in which the alveolar bone exists;

calculating at least one of a distance indicator, a volume indicator, a surface area indicator, a first moment indicator, a center-of-gravity indicator, and an alveolar bone indicator from the position data of the root apex, the alveolar crest, and the crown of the tooth; and measuring the progression of periodontal disease based on at least one calculated indicator, the method comprising at least one of the followings (1) to (5):

(1) the distance indicator being a value calculated as a ratio (DC/DF) of a length (DC) of the root surrounded by the alveolar bone currently supporting the tooth to a tooth length (DF) calculated based on the position data of the root apex, the alveolar crest, and the crown, said DF being automatically gained by the computer as the number of x-ray CT images corresponding to the entire tooth, said DC being automatically gained by the computer as the number of x-ray CT images corresponding from the root apex to the alveolar crest;

(2) the volume indicator being a value calculated as a ratio (VC/VF) of volume (VC) of the root surrounded by the alveolar bone currently supporting the tooth to tooth volume (VF) calculated based on the position data of the root apex, the alveolar crest, and the crown, said VF being automatically gained by the computer as a first sum of the numbers of pixels surrounded by first contour, the first contour being automatically detected by the computer as a contour from the root apex to the crown, said VC being automatically gained by the computer as a second sum of the numbers of pixels surrounded by second contour, the second contour being automatically detected by the computer as a contour the root apex to the alveolar crest;

(3) the surface area indicator being a value calculated as a ratio (SC/SF) of a surface area (SC) of the root surrounded by the alveolar bone currently supporting the tooth to a tooth surface area (SF) calculated based on the position data of the root apex, the alveolar crest, and the crown, said SF being automatically gained by the computer as a first sum of the numbers of pixels of a length of first contour, the first contour being automatically detected by the computer as a contour from the root apex to the crown, said SC being automatically gained by the computer as a second sum of the numbers of pixels of a length of second contour, the second contour being automatically detected by the computer as a contour from the root apex to the alveolar crest;

(4) first moment indicator being a value calculated as a ratio (MC/MF) of a first moment (MC) of the root surrounded by the alveolar bone currently supporting the tooth to a first moment (MF) of the tooth calculated based on the position data of the root apex, the alveolar crest, and the crown, said MF being automatically gained by the computer as a first summation of the area of first x-ray CT image times the length from the root apex, the first x-ray CT image being automatically detected by the computer as a x-ray CT image from the root apex to the crown, the area being gained by the computer as the number of pixels of the x-ray CT image, said MC being automatically gained by the computer as a second summation of the area of second x-ray CT image times the length from the root apex, the second x-ray CT image being automatically detected by the computer as a x-ray CT image from the root apex to the alveolar crest, the area being gained by the computer as the number of pixels of the x-ray CT image; and (5) the center-of-gravity indicator being a value calculated as a ratio (GC/GF) of the center of gravity (GC) of the root surrounded by the alveolar bone currently supporting the tooth to the tooth's center of gravity (GF) calculated based on the position data of the root apex, the alveolar crest, and the crown, said GF being automatically gained by the computer as dividing a first moment MF by mass, said MF being automatically gained by the computer as a first summation of the area of first x-ray CT image times the length from the root apex, the first x-ray CT image being automatically detected by the computer as a x-ray CT image from the root apex to the crown, the area being gained by the computer as the number of pixels of the x-ray CT image, said GC being automatically gained by the computer as dividing a second moment MC by mass, said MC being automatically gained by the computer as a second summation of the area of second x-ray CT image times the length from the root apex, the second x-ray CT image being automatically detected by the computer as a x-ray CT image from the root apex to the alveolar crest, the area being gained by the computer as the number of pixels of the x-ray CT image.

2. The method for periodontal disease measurement according to claim 1, wherein the contour of the tooth is determined by at least one of:
   (1) a comparison between the roundness of the tooth and a standard feature value;
   (2) a curve passing around the centers of gravity of the teeth; and
   (3) an adjacent CT image.

3. The method for periodontal disease measurement according to claim 1, wherein the method comprises at least one of the following items (1) and (2):
   (1) the root apex, the alveolar crest, and the crown being determined by the standard feature values and corresponding portions of another tooth in the vicinity; and
   (2) the alveolar crest being determined by the alveolar bone around the contour.

4. The method for periodontal disease measurement according to claim 1, further comprising, upon detecting a dentition and providing a dental formula, projecting the dentition on a curved surface along the dentition to create and display a panoramic image, and superimposing and displaying the dental formula thereon.

5. The method for periodontal disease measurement according to claim 4, wherein the curved surface is a curved surface parallel to a tooth axis.

6. The method for periodontal disease measurement according to claim 1, wherein the dental formula is displayed using a plurality of different colors.

7. The method for periodontal disease measurement according to claim 1, further comprising, upon determining the degree of a disease of teeth and periodontal tissues based on the indicator, comparing the indicator with an indicator previously obtained.

* * * * *